United States Patent [19]

Gustafsson

[11] Patent Number: 5,447,165
[45] Date of Patent: Sep. 5, 1995

[54] METHOD FOR ASCERTAINING PREVAILING LUNG CONDITION AND A DEVICE

[76] Inventor: Lars E. Gustafsson, Badhusvägen 8, 165 70, Hässelby, Sweden

[21] Appl. No.: 211,227
[22] PCT Filed: Sep. 28, 1992
[86] PCT No.: PCT/SE92/00675
§ 371 Date: Mar. 25, 1994
§ 102(e) Date: Mar. 25, 1994
[87] PCT Pub. No.: WO93/05709
PCT Pub. Date: Apr. 1, 1993

[30] Foreign Application Priority Data
Sep. 27, 1991 [SE] Sweden .................... 9102812

[51] Int. Cl.$^6$ ............................. A61B 5/08
[52] U.S. Cl. .................................. 128/719
[58] Field of Search ................... 128/716, 719

[56] References Cited
U.S. PATENT DOCUMENTS
3,799,149  3/1974  Rummel et al. .
3,951,607  4/1976  Fraser .
4,333,476  6/1982  Downing, Jr. .
4,796,639  1/1989  Snow et al. ............... 128/719

*Primary Examiner*—Lee S. Cohen
*Assistant Examiner*—Brian M. Green
*Attorney, Agent, or Firm*—Burns, Doane, Swecker & Mathis

[57] ABSTRACT

The invention relates to a method and to apparatus for ascertaining the current function or condition of a lung or the lungs of a living subject (1) chosen for a lung function evaluation, by measuring (3) the nitrogen monoxide content (NO) of the expiration air. The amount of nitrogen monoxide formed in the lung or the lungs during the expiration phase of one or more respiratory cycles and/or the time-distribution of the amount of nitrogen monoxide is compared (5) with the maximal nitrogen monoxide content and/or the time-distribution (6) of the nitrogen monoxide content of the exhalation air delivered by a complete, or unimpaired, lung function of a living subject, wherein a deviation disclosed by the comparison (9, 11) is normally interpreted as an impairment of the lung function.

12 Claims, 1 Drawing Sheet

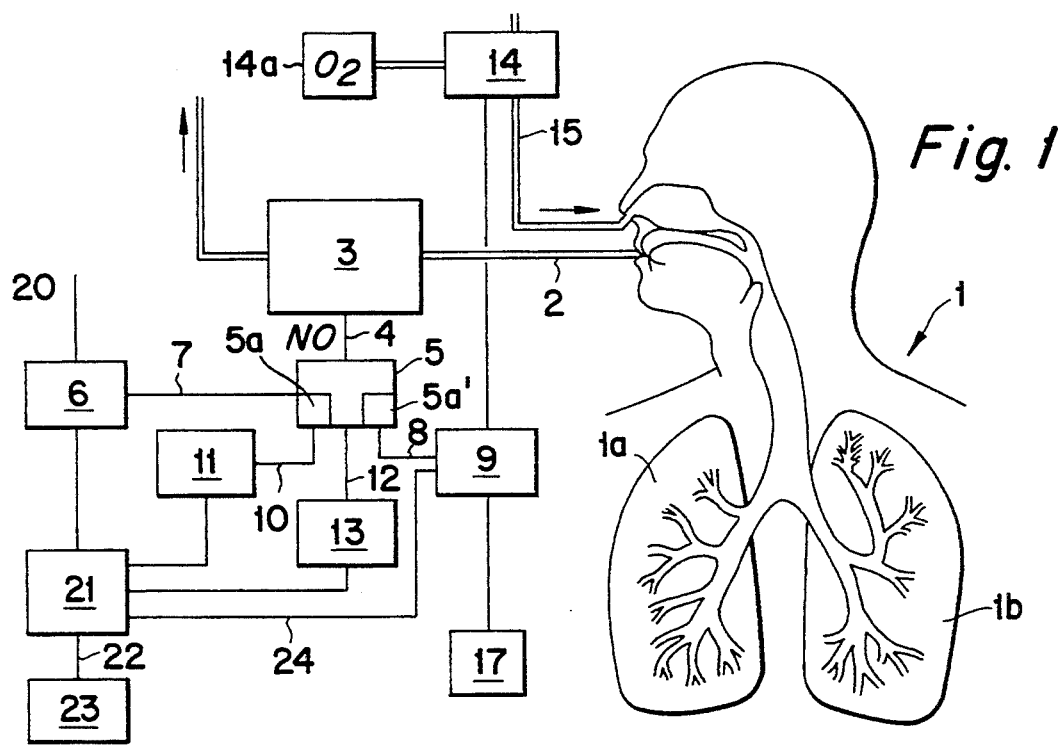
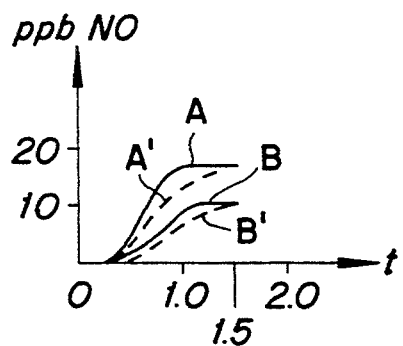
Fig. 2
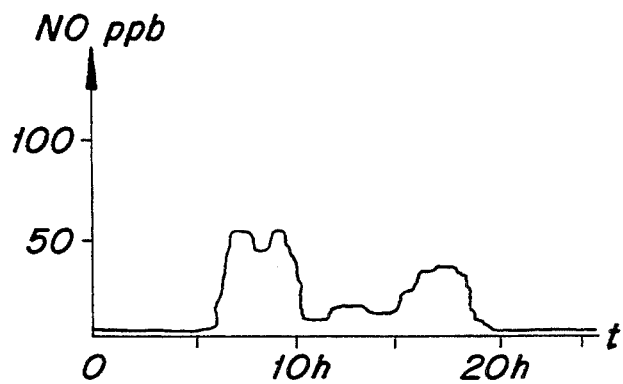
Fig. 3
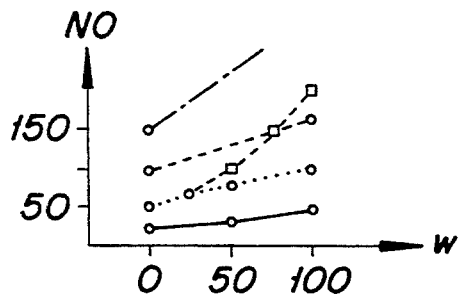
Fig. 4
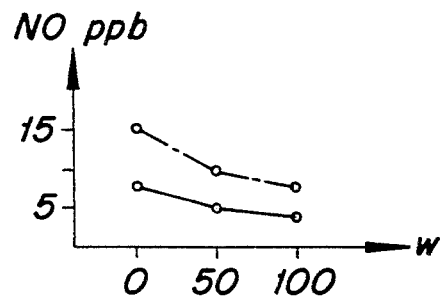
Fig. 5

METHOD FOR ASCERTAINING PREVAILING LUNG CONDITION AND A DEVICE

TITLE OF THE INVENTION

A method for Ascertaining Prevailing Lung Condition and a Device Herefor

1. Technical Field

The present invention relates primarily to a method of ascertaining the current condition of a lung or lungs of a living subject chosen for the purpose of ascertaining the lung condition of said subject, by measuring the nitrogen monoxide content of the exhalation air.

The invention also relates to a device for indicating and/or recording whether or not the current condition of a lung or lungs of a living subject chosen for the purpose of evaluating a lung condition is fully satisfactory or maximal or deviates from a maximal value, by measuring the nitrogen monoxide content of the exhalation air.

2. Known Prior Art

Since the present invention is based on evaluating the amount of nitrogen monoxide (NO) that is produced in living subjects that have a respiratory cycle, it can be mentioned by way of introduction that it is known that endothelium cells on the inner surfaces of blood vessels produce nitrogen monoxide in the body.

The Applicant has established that alveolar cells, the epithelium of the respiratory tract or any other cell that is in contact with air-containing parts of the lung produces endogenous nitrogen monoxide and that this nitrogen monoxide is secreted into the exhalation air. The Applicant has based the invention on this discovery.

The invention is also based on the evaluation of this formation of endogenous nitrogen monoxide in the lungs as a means for assessing the condition of the lungs, and on the understanding that this nitrogen monoxide can scarcely originate from other organs of the body, because, in such case, nitrogen monoxide would immediately bind to blood hemoglobin with subsequent decomposition.

The invention is also based on the understanding that the nitrogen monoxide content of exhalation air is influenced by different factors, such as by toxic bacteria, oxygen content or carbon dioxide content of the inhalation or exhalation gas.

In support of this conclusion, it can be mentioned that tests carried out in practice have shown clearly that the exhalation air contains measurable concentrations of nitrogen monoxide when the air inhaled is pure, and that the measurable production of nitrogen monoxide in the lungs can be blocked by nitrogen monoxide synthesis inhibitors.

Furthermore, animal experiments have shown that when blood circulation is stopped and the lungs ventilated with the aid of a respirator, the exhalation air still contains a measurable quantity of nitrogen monoxide. This indicates that the alveolar cells, respiratory tract mucus membrane or other cells in direct or close connection with the air-containing parts of the lung play an active roll in the formation of nitrogen monoxide, and that this occurs independently of or in addition to the earlier known formation of nitrogen monoxides in the endothelium cells and which has been considered to be stimulated by the blood flow.

Since the present invention is based on the ability to measure or assay relatively small quantities of nitrogen monoxide, it can be mentioned that the possibility of evaluating the nitrogen monoxide content of a gas with the aid of chemiluminescence techniques is already known, e.g. with the aid of Monitor Labs, 8840, NO/-$NO_2$ analyzer, retailed by Hässelvik AB, Cathrineholms gård, Katrineholm, Sweden.

Nitrogen monoxide (NO) can also be shown to exist in exhaled air by collecting the nitrogen monoxide in distilled water to which iron (II) sulphate is added, freeze-drying the water to dryness and thereafter showing the nitrogen monoxide in nitrite form, either by means of a diazo-reaction according to Martin, et al, or with the aid of a Niturtest[R] using a qualitative nitrite stick.

Earlier known measuring instruments operating with mass-spectrography can also be used for this purpose.

Since the present invention is concerned with assessing the current condition or function of a lung, it should be mentioned that it is previously known to be possible to ascertain the condition of a lung or the lungs of a living subject, such as a human being or an animal, by introducing intravenously a trace gas and then assessing the concentration and the time dispersement of the gas in the exhalation air of one or more respiratory cycles.

Since the present invention is concerned with ascertaining the current condition or function of a lung, it should also be mentioned that it is previously known to be possible to ascertain the condition or function of a lung or the lungs of a living subject, such as a human being or an animal, by causing the subject to inhale a trace gas and then measuring the concentration and time dispersement of the gas in the exhalation air. Nitrogen monoxide has been used as the trace gas.

Since the present invention is concerned with ascertaining the current condition or function of a lung, it should also be mentioned that it is previously known to be possible to ascertain the function or condition of a lung or the lungs of a living subject, such as a human being or an animal, by utilizing a trace gas produced in the body as a whole and thereafter measuring the concentration and time-distribution of the trace gas in the exhalation air. One such trace gas is carbon dioxide.

In such earlier known methods, the shape of the curve representative for the time-wise trace gas concentration of the exhalation air is decisive to the lung function or lung condition, wherein a steeper curve indicates a better lung capacity or condition than a flatter curve.

Other methods of determining the condition of lungs are also known to the art, examples of which are to be found in the following publications:

"Medicinsk fysiologi", Åke C Hjalmarsson, pages 185 to 195. Utbildningsförlaget, Stockholm. 1974.

"An introduction to Human Physiology", J. H. Green, pages 63 to 74, Oxford University Press, London. 1972. and "Textbook od Physiology, BDS", Donald Emslie-Smith et al, pages 127 to 139. Churchill Livingstone, Edinborough London Melbourne and New York 1988, which methods can be practiced when practicing the present invention.

DISCLOSURE OF THE PRESENT INVENTION

TECHNICAL PROBLEMS

When considering the earlier known standpoint of techniques, as described above, it will be seen that a technical problem resides in providing a method for ascertaining the current condition of a lung and in providing apparatus capable of indicating and/or recording the current condition of a lung or the lungs of a living subject selected for examination so as to determine whether the lung(s) of the subject concerned has (have) an unimpaired function or whether the lung or lungs deviate from a complete or maximal lung function, and in realizing the significance of measuring solely or essentially solely the occurrence and/or the time-distribution of the nitrogen monoxide content of the exhalation air during one or more exhalation phases of one or more respiratory cycles.

It will also be seen that a further technical problem resides in realizing that the nitrogen oxide content and/or the time-distribution of the content of nitrogen oxide formed in a lung or lungs (even though the term "an exhalation cycle" has been used, it will be obvious that several exhalation phases can be used so as to obtain a more accurate assessment) is of vital importance in establishing the current condition of a lung, and that a more qualified technical problem is one of realizing the necessity of comparing the evaluated nitrogen monoxide content and/or the time-distribution of the nitrogen monoxide content with the values of an unimpaired lung function with regard to the nitrogen monoxide content and/or the time-distribution of the nitrogen monoxide content applicable to a healthy or complete lung function.

It will also be seen that another technical problem is one of realizing that each discrepancy occurring when making said comparison of respective nitrogen monoxide contents, maximal total generated during an exhalation phase or the timewise distribution, shall normally be interpreted as an impaired lung condition or function, irrespective of whether the comparison gives a negative or a positive deviation.

An even more complicated technical problem is one of drawing certain well-found conclusions from a negative deviation and other well-found conclusions from a positive deviation.

It will also be seen that a technical problem resides in realizing that when a comparison of the nitrogen monoxide contents shows a negative value, the impaired lung condition or function can be readily compensated for by administering a larger or smaller quantity of oxygen gas and/or by taking measures to reduce the carbon dioxide content.

It will also be seen that another technical problem resides in the ability to realize that when the comparison of the nitrogen monoxide contents shows a positive value, the impaired lung condition or function can be compensated for, either totally or partially, by administering a slower or more prolonged treatment process, for instance by overcoming bacterial or other infectious influence, activating the immune defense system, reducing or fully eliminating the influence of irritating substances, chemical influence, and/or the effect of drug intake.

It will also be seen that another technical problem is one of realizing that an impaired lung condition or function can be compensated for by eliminating deviations in the time-distribution of the nitrogen monoxide content during an exhalation cycle. This can be achieved, for instance, by overcoming bacterial or other infectious influences, by activating the immunological defense system, by reducing or totally eliminating the effect of irritating substances chemical influence and/or the effect of drug intake.

Another technical problem is one of being able to realize those possibilities that are afforded when measuring the nitrogen monoxide content of the exhalation air when the patient is under different degrees of stress.

SOLUTION

With the intention of solving one or more of the aforesaid technical problems, the present invention is based on a method and a device for ascertaining the current condition or function of a lung or lungs or for indicating the current condition or function of a lung or lungs of a living subject chosen for evaluating lung condition or function, by measuring the nitrogen monoxide content of the exhalation air in a known manner.

According to the invention, the nitrogen monoxide content and/or the time-distribution of the nitrogen monoxide content formed in the lung or lungs during one (or more) exhalation phases shall be compared with a relevant corresponding nitrogen monoxide content and/or time-distribution of the nitrogen monoxide content applicable to the complete or unimpaired lung condition or function of a living subject, and by interpreting each deviation that occurs in said comparison as a more or less pronounced change, normally an impairment, in the condition or function of said lung or lung.

In the event that said deviation is manifested as a negative value between respective nitrogen monoxide contents, the present invention enables the impaired lung condition to be improved and to be fully compensated for by administering more or less oxygen gas to the inhalation air or by taking other measures which will reduce the carbon dioxide content.

In the event that the comparison between respective nitrogen monoxide contents is manifested in a positive value, it is not possible to improve or compensate for the impaired lung condition immediately, but that such improvement must be achieved by special treatment. For instance, such treatment may involve overcoming bacterial or other infectious influence, activation of the immunological defense system, taking measures to remove irritating substances, eliminating or reducing any chemical influence and the influence of administered pharmaceuticals.

However, when the comparison results in a flattening deviation in the time-distribution of the nitrogen monoxide content, the impaired lung condition can primarily be compensated for by overcoming bacterial or other infectious influences, by activating the immunological defense system, by eliminating or reducing the effect of irritating substances, by chemically retarding the influence of harmful immune reactions and of administered pharmaceuticals or drugs, by eliminating or reducing the influence of lung-cavity restricting or airflow restricting influences, or by eliminating or reducing the effect of G-forces or immersion, or dimensioning the influence of the blood flow through the lungs.

The invention also enables the function of a subject's lungs to be assessed with the subject under different degrees of stress.

ADVANTAGES

Those advantages afforded by the inventive method and inventive device primarily reside in the possibility of ascertaining the current condition or function of a lung or lungs solely by measuring the nitrogen monoxide content and/or the time-distribution of the nitrogen monoxide content of the exhalation air in a respiratory cycle.

The inventive method is mainly characterized by the features set forth in the following claim 1, whereas the inventive device is mainly characterized by the features set forth in the characterizing clause of the following claim 6.

BRIEF DESCRIPTION OF THE DRAWING

The invention will now be described in more detail with reference to an exemplifying embodiment thereof and with reference to apparatus constructed in accordance with the invention and functioning to indicate whether or not the current condition or function of a lung or lungs of a living subject chosen for evaluation of the subject's lung condition is complete or maximal or deviates from a standard value, by measuring the nitrogen monoxide content of the exhalation air in a respiratory cycle, and also the time-distribution of said nitrogen monoxide content. In the accompanying drawings, FIG. 1 is a schematic illustration which shows an inventive apparatus connected to the inhalation and exhalation phase of the respiratory cycle of a subject whose lung condition or function is to be ascertained;

FIG. 2 illustrates a number of examples of the nitrogen monoxide content and its time-distribution in the inhalation air expired in the exhalation phase of a respiratory cycle.

FIG. 3 is a time diagram which illustrates the concentration of nitrogen monoxide in the air of a large town or city;

FIG. 4 illustrates the variation in the endogenous secretion of nitrogen monoxide in response to an increasing level of stress in a number of persons; and FIG. 5 illustrates the amount of nitrogen monoxide secreted in response to an increase in the physical stress level of two of the persons shown in FIG. 4.

DESCRIPTION OF AN EXEMPLIFYING EMBODIMENT AT PRESENT PREFERRED

FIG. 1 illustrates schematically, and in section, the respiratory ducts of a person 1. The persons' lungs are referenced 1a and 1b.

The inventive device includes a tube 2 for exhalation gas which is connected to measuring apparatus 3, suitably the kind of apparatus described in the introduction. Particularly suitable apparatus in this regard are mass-spectrometers or those which operate with chemiluminescence.

Since such apparatus are known to the art, their construction and manner of operation will not be described in detail here.

A signal which is significant, such as directly proportional, to the nitrogen monoxide content of the exhalation air is sent to a comparator 5 over a line 4.

A reference signal corresponding to a normalized nitrogen monoxide content of the relevant person 1, such as the maximal nitrogen monoxide content, the total amount of nitrogen monoxide generated during an exhalation phase, and/or the timewise distribution, applicable to an unimpaired lung condition or function is sent to the comparator 5 from a device 6, over a conductor or line 7.

It also lies within the scope of the invention to store in the device 6 data that corresponds to the time-distribution or the like of a normalized nitrogen monoxide content.

When the comparison, for instance the comparison between a stored normalized maximal value and the instantaneous measured maximal value results in a negative value, a signal is sent to a device 9 on the line 8, via a device 5a'.

Should the value resulting from the aforesaid comparison be positive, a signal is sent to a device 11 on a line 10, via a device 5a. Should the value resulting from the aforesaid comparison be zero or close to zero, a signal is sent to a device 13 on a line 12, to indicate an unimpaired lung condition or function.

Each deviation disclosed by the comparison will normally be taken to indicate an impairment of the lung condition. It is necessary to take some degree of care, because the changes are not clear, but dependent on the individual concerned.

Thus, in the apparatus illustrated in FIG. 1, the first device 3, or measuring apparatus, may be intended to ascertain the current maximal nitrogen monoxide content and/or the time-distribution of the nitrogen monoxide content of an exhalation phase of a lung respiratory cycle. The resultant value or values applicable to the curve configuration are intended to be compared in the comparator 5 with a reference value corresponding to a normalized maximal nitrogen monoxide content and/or a normalized time-distribution of the nitrogen monoxide content for an unimpaired lung condition of a person 1, wherein the reference value pertaining to the time-distribution of the normalized nitrogen monoxide content is delivered from the device 6 in which said measuring values are stored.

As before mentioned, each deviation shown by the aforesaid comparison of the respective maximal values is interpreted as being indicative of an impaired lung function, this interpretation being effected in third devices 5a, 5a'.

With reference to FIG. 1, when the comparison made in the first circuit 5a' between said maximal values results in a negative value, a device 14 connected to the source of inhalation air is activated by the device 9 in a manner to introduce a greater or lesser quantity of oxygen gas to the inhalation air, through a pipe 15, from a container 14a, the amount of oxygen gas administered being dependent on the magnitude of said negative value.

The device 9 will preferably also be capable of controlling a device 17 in a known manner such as to control means for creating conditions which will reduce the carbon dioxide content.

When the comparison made between the maximal nitrogen monoxide contents in the circuit 5a shows a positive value, the impaired lung function can be compensated for by administering a slower or more prolonged form of treatment. This treatment may comprise overcoming bacterial or other infectious influences, activation of the immunological defense system, the retardation of harmful immune reactions, the reduction or elimination of the influence of irritating substances, chemical effect, and the regulation of the quantities in which pharmaceuticals are administered.

The comparison between the nitrogen monoxide time-distribution of the nitrogen monoxide content can be effected in different ways, although this comparison requires measuring apparatus of a more complicated nature.

However, the manner in which the devices represented by the boxes in FIG. 1 shall be constructed in order to function in accordance with the aforedescribed processes or procedures will be obvious to one of normal skill in this art, and consequently these processes and procedures will not be described in detail.

FIG. 2 is a graph which shows two different applications, where the maximal nitrogen monoxide content of the exhalation air of a first person A is different to the maximal nitrogen monoxide content of the exhalation gas of a second person B.

The full line "A" is intended to illustrate the standard maximal nitrogen monoxide content and the standard time-distribution of the nitrogen monoxide content of the exhalation gas exhaled by a person 1 whose lung function is unimpaired.

The broken line A' is intended to illustrate an impairment in the current lung function, since the time-distribution of the nitrogen monoxide content deviates (flattens-out slightly) from the ideal time-distribution "A", although it is assumed that the maximal value is the same for both curves.

The graph shown in FIG. 2 also includes a standard curve B and a curve B' which is representative of an impaired lung function of the person concerned.

The illustrated apparatus includes a fourth device 21 (separated somewhat from the device 5) which enables a deviation or deviation to be established between the time-distribution of the nitrogen monoxide content of the current, normalized lung function via the line 4 and the standard value inserted via the line 7, and when the time-division of respective nitrogen monoxide contents coincide mutually within predetermined tolerance limits, there is sent on the line 24 a signal which indicates complete or unimpaired lung function, whereas if the comparison shows a significant deviation in the time-distribution of the nitrogen monoxide content, there is delivered on line 22 a signal which indicates the structure of the impaired lung function in a device 23.

It should normally be possible to compensate for such an impairment by overcoming bacterial or other infectious influences, by activating the immunological defense system, by retarding harmful immune reactions, by reducing or eliminating the effect of irritating substances, chemical influence and the effect of administered pharmaceuticals, or by correcting the proportional intake and mixture of such pharmaceuticals.

In the FIG. 1 illustration, the inhalation air and exhalation gas have been mutually separated for clarity reasons and in practical applications both the inhalation air and exhalation gas may pass either through the mouth or the nose.

The curves in FIG. 2 are shown in a simplified form. In practice, the slope may vary and the curve may be displaced laterally, and thus an accurate analysis is required in order to evaluate the significance of a changed curve form.

It will be understood that the invention is not restricted to the aforegoing and that the illustrated apparatus may be modified in several respects and can also be applied in other aspects, of which a number are described below.

It lies within the scope of the invention to administer pharmaceuticals in a controlled manner by inhalation or via the blood, and to administer pharmaceuticals, or drugs, through body orifices in a known manner with the intention of elevating the level of the maximal nitrogen monoxide content. There may be used to this end an agent designated "substance P" and a substance designated "Carbachol".

The maximal nitrogen monoxide level can be lowered and the curve form changed by administering a nitrogen monoxide synthesis inhibitor, such as nitroarginine.

The amount and/or concentration of endogenously generated nitrogen monoxide is thus influenced by the conditions that prevail in the respiratory ducts and/or lungs, by blood circulatory conditions in the lungs and administered pharmaceuticals.

The amount or concentration of endogenous nitrogen monoxide in the expiration air in a respiratory cycle is thus a measurement of the lung condition or function and can be considered to provide a better method than those earlier used, at least insomuch that no exogenous nitrogen monoxide need be supplied for the measurements.

In comparison with carbon dioxide, the measured nitrogen monoxide has the advantage that it is a gas which is produced in lungs and respiratory tracts rather than in the remainder of the body, thereby providing an understanding of the specific metabolic disorder in the lungs or along the respiratory tracts and how this gas is excreted into the exhalation gas.

The invention can be said to produce a rapid "on-line" (immediate) activity in an enzyme system or a group of enzymes of significance to the immunological defense system, circulation regulation and the nervous system.

The invention is able to quickly indicate the influence of foreign substances or particles in the air inhaled, for instance irritating or allergy-promoting substances, aspiration, cytostatic, immune-influenced processes.

The invention also enables the influence of physical factors on the lungs to be assessed, for instance such factors as burn damage, cold damage and oxygen deficiency.

The invention also enables the effect of infectious organisms to be measured, or the toxicity of such organisms or the effect of their toxic substances through the influence of body substances.

The invention can also be used as an indicator of adequate oxygenation and carbon dioxide level in conjunction with respirator treatment.

The invention can also be used as an indicator on the degree of seriousness of bleeding trauma or shock.

The invention can also be used to measure activation of the immunological defense system against tumor cells or response to infectious diseases in the respiratory tracts.

The invention can also be used to measure the degree of congestion of the lung function, for instance due to liquid or gas or foreign bodies, pulmonary oedema or rigid thorax, tumors in thoracic cavities or the abdomen, upward pressure from the abdomen and obstructive lung function encroachment, e.g. caused by tumors or foreign bodies in the respiratory ducts or swelling of the mucus membrane and the production of phlegm in such diseases as asthma or bronchitis, emphysema, etc.

The invention can also be used to measure the predestination of or occurrence of oxygen deficiency response towards altitude sickness.

The invention can also be used to measure overdosing of oxygen, either when administered at normal ambient pressure, for instance in the case of respirator treatment, or when applying oxygen therapy to newly-born babies or when hyperbaric breathing in conjunction with deep sea diving, for instance.

The invention can also be used to determine uneven distribution (tolerable or intolerable) of the airflow in the lung in relation to the blood flow, either as a result of the position of the body (long-term bed patients), narcosis, increased or decreased or otherwise changed gravitational forces when flying, space flights, immersion in liquid.

Since carbon dioxide lowers the nitrogen monoxide content and carbon dioxide is a gas which has a narcotic capability, it can be expected that other narcotic gases can also influence the nitrogen monoxide content of the exhalation gas, and it should therefore be possible to monitor the effects of narcotic gases on the body by monitoring the nitrogen monoxide content of exhalation air and the time-distribution of nitrogen monoxide therein.

In addition to evaluating the maximal concentration of nitrogen monoxide or the timewise distribution during an exhalation phase of a respiratory cycle in accordance with the aforegoing, it also lies within the purview of the invention to evaluate other parameters. For instance the inventive method can be used to evaluate the time-wise concentration of nitrogen monoxide after a maximum value before the exhalation phase has been completed.

It is also possible to evaluate the concentration of nitrogen monoxide in relation to movement of the thorax and in relation to the volume of gas exhaled, (irrespective of what it comprises), or in relation to the outflow or the time-dependent concentration of another indicator gas.

In the case of the FIG. 2 embodiment, data relating to a selected degree of stress or strain can be delivered to the device 6 on a line 20. A measurement value deviation and chosen stress-degree evaluating and receiving device 21 is intended to record any deviation that may occur and a stress degree marking.

FIG. 3 is a time diagram representative of the concentration of nitrogen monoxide in the air, while FIG. 4 shows the variation in the excretion of endogenous nitrogen monoxide as a result of an increase in the physical exertions of a number of persons or subjects, and FIG. 5 illustrates the amount of nitrogen monoxide excreted by two of the subjects of FIG. 4 as a result of greater physical exertions.

For a deeper insight in this regard, reference is made to the teachings of Swedish Patent Application filed on the Nov. 4, 1991.

It will be understood that the invention is not restricted to the aforedescribed exemplifying embodiment and that modifications can be made within the scope of the inventive concept as defined in the following Claims.

I claim:

1. A method of ascertaining the current function or condition of at least one lung of a living subject selected for a lung evaluation, comprising the steps of:
   measuring a nitrogen monoxide content of expiration air,
   comparing at least one of the nitrogen monoxide content and a time-distribution of the nitrogen monoxide content of the gas generated in said at least one lung during at least one exhalation phase with at least one of a maximal nitrogen monoxide content and a time-distribution of the maximal nitrogen oxide content of a living subject having an unimpaired lung function, and
   interpreting a deviation manifested by said comparison as an impaired lung function.

2. A method according to claim 1, comprising the further step of, when the comparison between said nitrogen monoxide contents shows a negative value, administering oxygen in inhalation air to compensate the impaired lung function.

3. A method according to claim 1, wherein, when the comparison between said nitrogen monoxide contents shows a positive value, compensating the impaired lung function by at least one of the following procedures: overcoming bacterial or other infectious influence, activating the immunological defense system, retarding harmful immune reactions, reducing or eliminating the effect of irritating substances or chemical influences, regulating the amounts in which pharmaceuticals are administered, and correcting the rate at which said pharmaceuticals are administered.

4. A method according to claim 1, wherein, when a deviation in the time-distribution of the nitrogen monoxide content has been interpreted, compensating the impaired lung function by at least one of the following procedures: overcoming bacterial or other infectious influence, activating the immunological defence system, retarding harmful immune reactions, reducing or eliminating the effect of irritating substances or chemical influences, regulating the amount in which pharmaceuticals are administered, and changing the rate at which such pharmaceuticals are administered.

5. A method according to claim 1, comprising the further step of, when the comparison between said nitrogen monoxide contents shows a negative value, taking measures to reduce the carbon dioxide content in inhalation air to compensate the impaired lung function.

6. A method of ascertaining the current function or condition of at least one lung of a living subject selected for a lung evaluation when said at least one lung is under different degrees of physical stress or strain, comprising the steps of:
   measuring a nitrogen monoxide content of expiration air,
   comparing the amount of nitrogen monoxide that is contained in said at least one lung of said subject during an exhalation phase of at least one respiration cycle while the subject is under a predetermined degree of stress or strain with a corresponding amount of nitrogen monoxide contained in at least one lung of a reference subject having a predetermined lung condition essentially at the same degree of stress or strain, wherein a deviation resulting from the comparison is interpreted as a changed lung function or condition.

7. An apparatus for indicating whether or not a current lung function or condition of at least one lung belonging to a living subject chosen for evaluation of lung function is unimpaired, maximal, or deviates from a maximal value, comprising:
   means for measuring a nitrogen monoxide content of exhalation air,
   a first device, operatively connected to said measuring means, for evaluating at least one of a current nitrogen monoxide content and a time-distribution of the nitrogen monoxide content during an exhalation phase of a lung respiratory cycle,
   a second device, .operatively connected to said first device, in which at least one value obtained by said first device is compared with at least one of a maximal nitrogen monoxide content and a time-distribution of the nitrogen monoxide content pertaining to an unimpaired lung of a living subject; and
   a third device, operatively connected to said second device, in which each deviation manifested by said comparison is interpreted as an impaired lung function.

8. An apparatus according to claim 7, further comprising means for compensating, when the comparison between nitrogen monoxide contents gives a negative value, the impaired lung function by administering oxygen in inhalation air.

9. An apparatus according to claim 7, further comprising means for compensating, when the comparison between nitrogen monoxide contents shows a positive value, the impaired lung function by one of the following procedures: overcoming bacterial or other infectious influence, activating the immunological defense system, retarding harmful immunoreactions, reducing or eliminating the influence of irritating substances or chemicals, regulating the amount in which pharmaceuticals are administered, and changing the rate at which such pharmaceuticals are administered.

10. An apparatus according to claim 7, further comprising means for evaluating a deviation in the time-distribution of the nitrogen monoxide content, wherein the impaired lung function is compensated by following at least one of the following procedures: overcoming bacterial or other infectious influences, activating the immunological defense system, retarding harmful immune reactions, reducing or eliminating the effect or irritating substances or chemical influences, regulating the amounts in which the pharmaceuticals are administered, changing the rate at which said pharmaceuticals are administered, supplying blood or draining blood, and any other measure which will regulate the liquid balance.

11. An apparatus according to claim 7, further comprising means for compensating, when the comparison between nitrogen monoxide contents gives a negative value, the impaired lung function by taking measures to reduce the carbon dioxide content in inhalation air.

12. An apparatus for ascertaining the current lung function or condition of at least one lung of a living subject chosen for evaluation of the lung under different degrees of stress or strain, comprising:

means for measuring a nitrogen monoxide content of exhalation air, first means for determining the current amount of nitrogen monoxide present in the exhalation air of at least one respiration cycle with the lungs of the subject under a predetermined degree of physical stress or strain.

second means for comparing said determined amount of nitrogen monoxide to an amount of nitrogen monoxide obtained from another subject whose lung condition or function is known wherein said other person is under essentially the same degree of physical stress or strain, and third means for interpreting each deviation disclosed by the comparison as one of a deterioration of and an improvement in the lung condition or lung function.

* * * * *